(12) United States Patent
Berry et al.

(10) Patent No.: US 6,293,958 B1
(45) Date of Patent: Sep. 25, 2001

(54) CATHETER HAVING FLOW DIFFUSING TIP

(75) Inventors: David Berry; David R. Holmes; Robert S. Schwartz, all of Rochester; Robert A. VanTassel, Excelsior, all of MN (US)

(73) Assignee: Acist Medical Systems, Inc., Eden Prairie, MN (US)

( * ) Notice: Subject to any disclaimer, the term of this patent is extended or adjusted under 35 U.S.C. 154(b) by 0 days.

(21) Appl. No.: 09/123,807

(22) Filed: Jul. 27, 1998

(51) Int. Cl.[7] .................................................... A61M 29/00
(52) U.S. Cl. ............................ 606/191; 606/192; 604/264
(58) Field of Search ........................................ 606/191, 192, 606/193, 194–198, 107, 108; 604/264, 28, 53, 9, 96, 164, 247, 246, 245; 128/204.24, 912

(56) References Cited

U.S. PATENT DOCUMENTS

| 4,961,731 | 10/1990 | Bodicky et al. . | |
| 4,995,863 | * 2/1991 | Nichols et al. | 604/247 |
| 5,085,635 | * 2/1992 | Cragg | 604/96 |
| 5,085,636 | * 2/1992 | Burns | 604/99 |
| 5,163,928 | 11/1992 | Hobbs et al. . | |
| 5,224,983 | * 7/1993 | Fenton, Jr. | 604/247 |
| 5,250,034 | 10/1993 | Appling et al. . | |
| 5,267,979 | 12/1993 | Appling et al. . | |
| 5,616,137 | 4/1997 | Lindsay . | |
| 5,807,349 | * 9/1998 | Person et al. | 604/247 |

* cited by examiner

Primary Examiner—Henry J. Recla
Assistant Examiner—Lien Ngo
(74) Attorney, Agent, or Firm—Oppenheimer Wolff & Donnelly, LLP

(57) ABSTRACT

An intravascular catheter having a flow diffusing distal tip includes a plurality of cuts formed through the tubular wall thereof so as to define a plurality of generally U-shaped flaps, the flaps being disposed in at least one and preferably two axially displaced bands. When contrast fluid or the like is injected under pressure into the proximal end of the catheter, the flow of the liquid exits the openings in which the plurality of flaps are hinged, causing the flaps to vibrate and effectively eliminate any tendency for the contrast media to be expelled as a jet from the open distal end of the catheter. Having an open distal end allows the catheter to be passed over a guidewire.

19 Claims, 3 Drawing Sheets

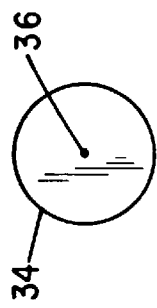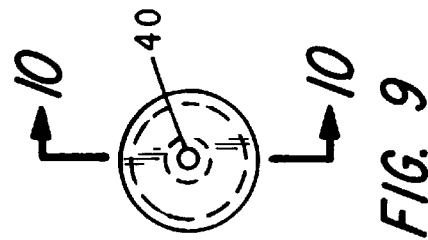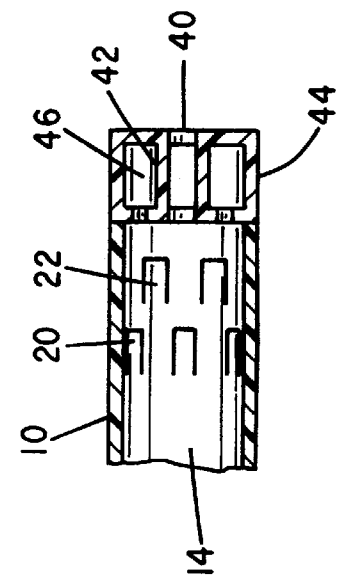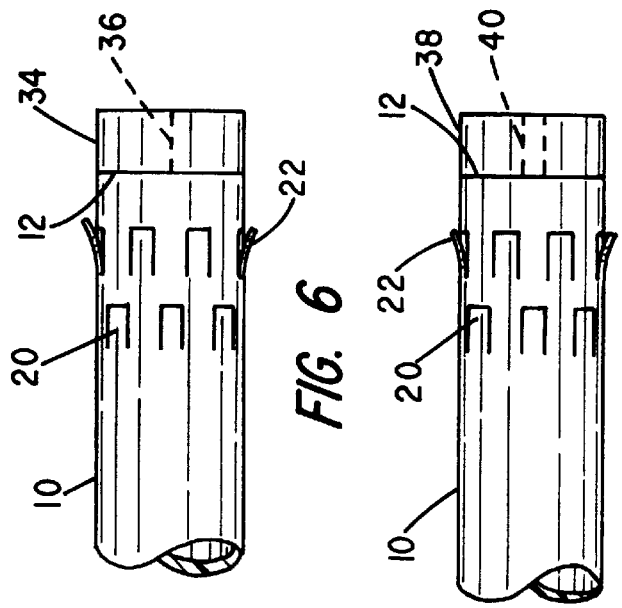

CATHETER HAVING FLOW DIFFUSING TIP

BACKGROUND OF THE INVENTION

1. Field of the Invention

The present invention relates generally to angiographic and other diagnostic or therapeutic catheters and more particularly to a feature of such catheters which prevents high velocity jetting of contrast media, fluid or the like from the distal end opening of such catheters.

2. Discussion of the Prior Art

In diagnostic catheters designed for left ventricular injection of contrast media or dyes or for higher pressure injections into coronary arteries during angiographic and therapeutic procedures, the outside diameter of such catheters is necessarily small, typically in the range of from 3 to 10 Fr. When it is considered that radiographic contrast media is commonly injected at a rapid rate by means of either a power injector or by hand, the liquid contrast media exits the distal end opening of the catheter as a high velocity jet. This may cause "whipping" of the catheter tip and resulting damage to delicate endothelial tissues lining the blood vessels being examined. The velocity and impact of the jet itself may be sufficiently high to damage the vessel wall. Experience has shown that such tissue damage may form the nidus of stenotic lesions and dissections and ultimately to occlusion of such blood vessels.

As is pointed out in the introductory portion of the Cragg Patent U.S. Pat. No. 5,085,635, to minimize undesirable effects of the high velocity jet, prior art catheter designs had sealed distal ends with a plurality of side holes near the distal end to allow the contrast media to exit in a radial direction through several ports, thereby reducing somewhat the overall velocity of the exiting contrast liquid. Even here, it was often too high. Having a closed distal end effectively precluded such catheters from being fed over a guidewire. This, of course, makes it difficult and sometimes unsafe to appropriately place the distal end of the catheter prior to contrast ejection. To address this problem, the angiographic catheter particularly described in the Cragg '635 patent incorporates a normally completed closed leaflet valve arrangement over the end hole of the catheter which permits passage of a guidewire therethrough, but which effectively blocks the flow of contrast media therethrough. Thus, the contrast media exits a plurality of apertures formed through the wall of the catheter tubing proximate the distal end thereof.

SUMMARY OF THE INVENTION

The intravascular catheter of the present invention is adapted to provide higher volume flow through a relatively small lumen and with a reduced exit flow velocity than with conventional, prior art catheters for the same purpose. The catheter comprises an elongated, flexible, tubular body member having a proximal end, a distal end and a lumen extending therebetween. A plurality of circumferentially spaced cuts or slits are formed through the wall of the tubular body member to the lumen so as to define a plurality of hinged flaps that are symmetrically arranged such that flow of a stream of fluid through the lumen above a predetermined velocity causes the hinged flaps to vibrate in and out of the stream to diffuse it and to dissipate the kinetic energy of the fluid. The contrast fluid not only exits the distal end opening of the catheter at a greatly reduced velocity, but also, the contrast fluid exits through the ports defined by the flaps to effectively create a diffuse cloud of contrast fluid surrounding the distal tip portion of the catheter. The symmetric placement of the flap covered openings also distributes the Newtonian forces acting on the tip by the existing fluid so that no whipping occurs. The distal end may be open or may include a short segment having a virtual opening that is normally closed to block flow of contrast fluid from the distal end of the catheter, but which may allow the passage of a guidewire therethrough. Alternatively, the short tip segment may have a longitudinal bore for receiving a guidewire therealong, but the bore is made to close to prevent flow of contrast fluid out the distal end of the short tip segment due to the pressure of the contrast fluid present within that tip segment.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

FIG. 6 is a partial side elevation view of the distal end portion of a catheter constructed in accordance with yet another embodiment of the invention;

FIG. 7 is a distal end view of the catheter of FIG. 6;

FIG. 8 is a partial side elevation view of a catheter constructed in accordance with a still further embodiment of the invention;

FIG. 9 is a distal end view of the catheter of FIG. 8; and

FIG. 10 is a cross sectional view taken along the line 10—10 in FIG. 9.

DESCRIPTION OF THE PREFERRED EMBODIMENT

Figure 1:
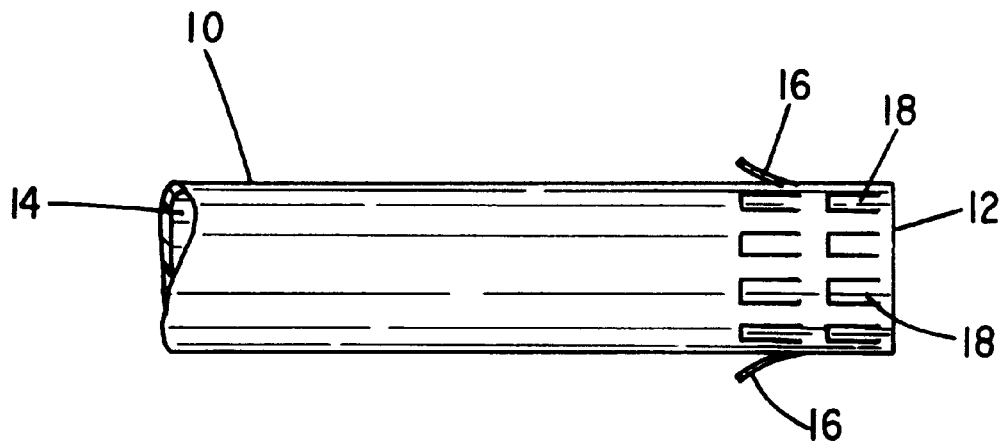
FIG. 1 is a side elevational view of the distal end portion of an intravascular catheter constructed in accordance with one embodiment of the invention.

Referring to FIG. 1 for purposes of illustration, there is shown a greatly enlarged view of the distal end portion of an angiographic catheter used to inject a contrast media into a target coronary blood vessel so that the blood vessel lumen can be visualized. It comprises an elongated, flexible plastic tubular body member 10 having a proximal end (not shown), a distal end 12 and a lumen 14 extending therebetween. The catheter body may typically be approximately 100 cm in length and may have an outside diameter typically in the range of from about 3 to 10 Fr and an inside diameter of about 0.046 in. The distal end 12 is open and, accordingly, the catheter may be passed over a guidewire as it is being routed through the vascular system and into a selected coronary blood vessel.

As mentioned above, intravascular catheters are often used for injecting liquids into selected vasculature. The catheter tip striking the wall of the blood vessel can result in trauma injury to it. In addition, the relatively high velocity jet has sufficient kinetic energy to itself introduce damage to the wall of the blood vessel. To obviate this problem, in accordance with the present invention, there is provided a means for diffusing the high velocity flow exiting the distal end 12 of the catheter.

As shown in FIG. 1, there is formed through the side wall of the catheter body 10 a series of three-sided cuts or slits that define a plurality of generally U-shaped hinged flaps, as at 16, that are circumferentially and regularly spaced about the catheter. Two such slits may be made to intersect to create a triangular flap if desired. The high velocity flow of fluid through the catheter results in a Bernoulli effect pressure drop within the lumen of the catheter such that the hinged flap 16 will tend to deform through the three-sided opening defined by the cuts and enter the space occupied by the lumen and thereby disrupt the liquid flow stream. Tests have been conducted and reveal a tendency for the flaps to vibrate, which is believed to be possibly due to the combined opposing forces on the flaps caused by the Bernoulli effect in reducing the pressure within the lumen of the catheter and the impact force of the liquid on the flaps. As the flaps oscillate, they consume kinetic energy as they move in and out of the lumen. The kinetic energy and, thus, the velocity of the fluid stream is reduced. Further, contrast media flows out through the openings when the flaps are deflected to effectively increase the volume and, thus, reduce the pressure and the velocity of the liquid stream leaving the open distal end of the catheter.

There is also illustrated in FIG. 1 a second circumferential band of individual U-shaped flaps 18. They are preferably staggered relative to the circumferential band of flaps 16 and further add to breaking up the high velocity jet that might otherwise exit the catheter. In the arrangement of FIG. 1, the flaps are cut so as to have their trailing edges as hinges causing the exiting contrast fluid to be in the retrograde direction.

Figure 2:
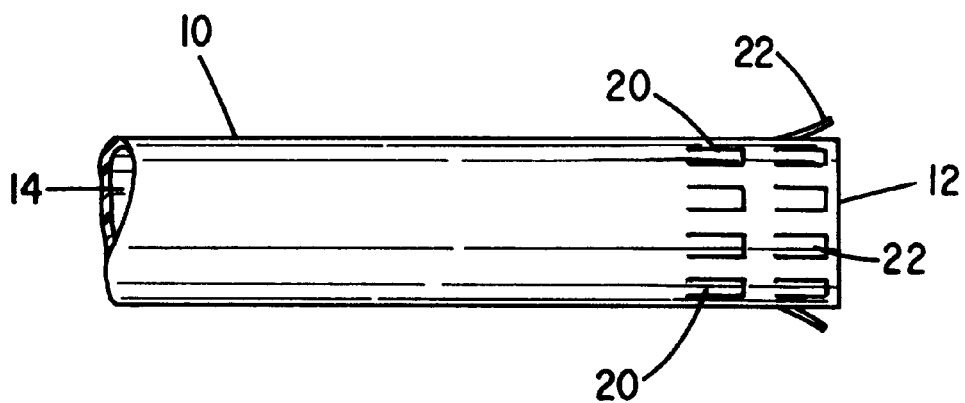
FIG. 2 is a side elevational view of the distal end portion of a catheter constructed in accordance with another aspect of the invention.

In FIG. 2, the U-shaped, hinged flaps are cut so that the leading edges thereof comprise the hinges and with this pattern, fluid exiting the apertures defining the flaps is in an antegrade direction and at an angle to the longitudinal axis of the catheter.

Figure 3:
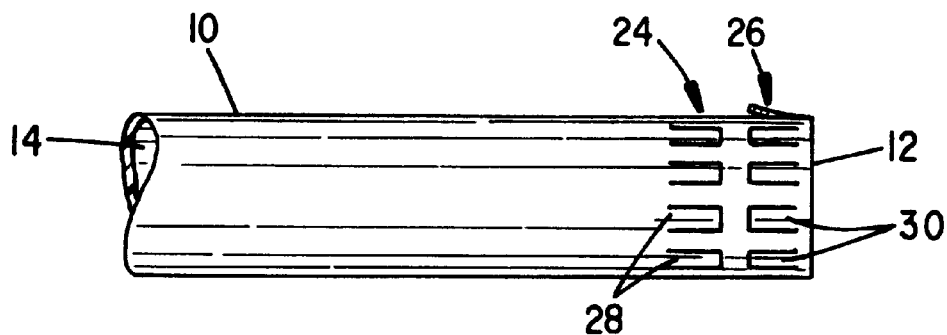
FIG. 3 is a side elevational view of the distal end portion of a catheter constructed in accordance with a further embodiment of the invention.

To produce still further enhanced diffusion of the liquid flow stream exiting the distal end 12 of the catheter, the three-sided flaps in a circumferential band 24 may have their hinge edges located proximally and the flaps in the circumferential band 26 having their hinge edges located distally as shown in FIG. 3. The vibrating flaps 28 and 30 in the respective bands 24 and 26 move in and out of the flow stream, reducing its kinetic energy and also the fluid exiting the apertures defining the flaps tend to flow in opposite directions upon exiting the lumen to collide and create a desired distribution pattern about the distal end portion of the catheter which may be characterized as a confused, turbulent broken flow as distinguished from a jet.

Figure 4:
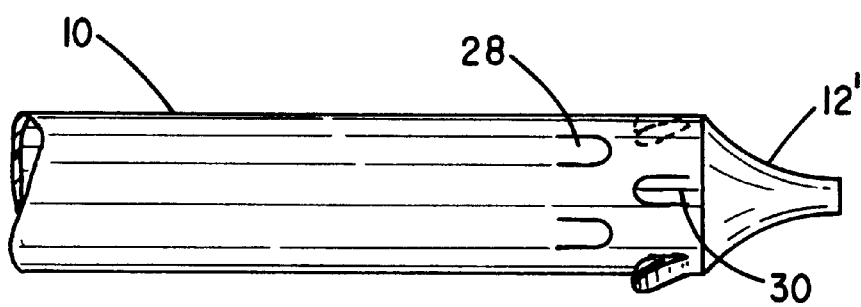
FIG. 4 is a side elevational view of the distal end portion of a catheter constructed in accordance with a still further embodiment of the invention.
Figure 5:
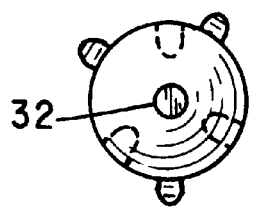
FIG. 5 is a distal end view of the catheter of FIG. 4.

To further reduce any propensity of the diagnostic catheters constructed in accordance with the present invention to allow distal end jetting, it has been found expedient to thermally mold the soft distal tip of the plastic catheter down on a solid mandrel so that there is just a small, expandable hole 32 left in the end through which a guidewire may be passed. In accordance with Poisseuilles' Law, the hydraulic resistance to liquid flow through a pipe is proportional to the inverse 4th power of the radius ($1/r^4$). Thus, in the arrangement shown in FIGS. 4 and 5, the resulting high resistance greatly impedes outflow of liquid through the opening 32 and the pressure is relieved by liquid flow out through the openings defining the vibrating flaps 28 and 30 that are located proximal of the formed distal end 12' of the catheter. When the guidewire is withdrawn, the area of the opening defined by aperture 32 decreases due to the elastic nature of the plastic itself and because of the Bernoulli force due to the flow of fluid through the orifice causing a pressure differential.

Another approach to eliminating end-jetting of contrast fluid from the catheter is illustrated in the further embodiments depicted in FIGS. 6–10. In the embodiment illustrated in FIG. 6, there is secured to the distal end 12 of the catheter 10 a soft elastomeric tip member 34 having a virtual opening 36 formed therethrough. The virtual opening 36 is normally closed to prevent any appreciable flow of contrast liquid or the like beyond the distal end 12 of the catheter. However, the elastomeric material from which the tip member 34 is formed is sufficiently resilient such that a guidewire (not shown) can be pushed through the virtual opening 36 with the tip member 34 forming a seal about the perimeter of the guidewire.

In the embodiment illustrated in FIGS. 8–10, the catheter body 10 again has a tip member 38 affixed to its distal end 12, the tip member preferably being molded or created in an extrusion process from a resilient, soft, elastomeric material such as silicone rubber or polyurethane. The tip member 38 is appropriately bonded to the catheter body 10 and includes a central opening 40 of a diameter that may be somewhat larger than the diameter of any guidewire that is to be used in the routing and placement of the catheter within the vascular system. An inner tubular wall 42 cooperates with an outer wall 44 of the tip member to define an annular chamber 46 which is in fluid communication with liquids injected into the lumen 14 of the catheter body 10. The wall 42 is designed to be compliant and when liquid under pressure is injected into the catheter system, the walls 42 deform inwardly to close the opening 40, preventing the pressurized liquid from exiting the distal end of the catheter.

In the embodiments of FIGS. 6–10, the respective tip members 34 and 38 may have a length in the range of from 0.5 to 4 mm and typically will have an outside diameter corresponding to that of the catheter body 10 to which it is affixed. It is also contemplated that in the case of the embodiment of FIGS. 8–10, the chamber 46 may be filled with a porous, expandable polymer that when subject to the contrast liquid under high pressure will expand to seal off the guidewire lumen actively during the injection process.

With no limitation intended, for a diagnostic catheter having an outer diameter of 5 Fr., the catheter may be slit to form three to five flaps in each band, where the flaps are approximately one mm in width and one mm long. The resulting openings through which the flaps move are sufficient to reduce the velocity of the contrast media or other liquid exiting the openings and the distal tip. Impingement of the liquid on the flaps also redirects the flow and enhances interference between the plural steams exiting the multiple openings, further reducing the effective kinetic energy of the exiting liquid.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. An intravascular catheter, comprising:
   (a) an elongated, flexible tubular body member of a predetermined diameter and wall thickness, the tubular body member having a proximal end, a distal end and a lumen extending therebetween; and
   (b) a plurality of circumferentially spaced cuts formed through the wall thickness of the tubular body member to said lumen to define a plurality of vibratable flaps sufficiently deformable such that a flow of a stream of fluid through the lumen above a predetermined velocity causes the vibratable flaps to oscillate into the lumen and out of the lumen, the vibratable flaps extending outwardly beyond the predetermined diameter of the flexible tubular body member when oscillating out of the lumen, the oscillation of the vibratable flaps diffusing the stream and dissipating kinetic energy of the stream, and the vibratable flaps having a hinged portion.

2. The intravascular catheter as in claim 1 wherein the tubular body member is tapered over a distal end portion thereof to a lesser diameter than the predetermined diameter of the remainder of the tubular body member to define a central opening adapted to receive a guidewire therethrough.

3. The intravascular catheter as in claim 1 wherein the circumferentially spaced cuts are disposed in first and second axially spaced annular bands.

4. The intravascular catheter as in claim 2 wherein the plurality of circumferentially spaced cuts are disposed in first and second axially spaced bands.

5. The intravascular catheter as in either claim 3 or claim 4 wherein the plurality of vibratable flaps deflect liquid in a retrograde direction.

6. The intravascular catheter as in claim 3 or 4 wherein the plurality of vibratable flaps deflect liquid in the antegrade direction.

7. The intravascular catheter as in either claim 3 or claim 4 wherein the plurality of flaps direct liquid flowing through openings defined by the circumferentially spaced cuts in both an antegrade and a retrograde direction.

8. An intravascular catheter, comprising:
   (a) an elongated, flexible, tubular body member of a predetermined diameter and wall thickness, the tubular body member having a proximal end, a distal end and a lumen extending therebetween;
   (b) a plurality of circumferentially spaced cuts formed through the wall thickness of the tubular body member to said lumen in a zone proximate the distal end of the body member to define a plurality of vibratable flaps sufficiently deformable such that a flow of a stream of fluid through the lumen above a predetermined velocity oscillates the vibratable flaps into the lumen and out of the lumen, the vibratable flaps extending outwardly beyond the predetermined diameter of the flexible tubular member when oscillating out of the lumen, the oscillation of the vibratable flaps diffusing the stream and dissipating kinetic energy of the stream, and the vibratable flaps having a hinged portion;
   (c) a tip member affixed to the distal end of the tubular body member, the tip member having a passageway therethrough adapted to receive a guidewire therein with the passageway being self-sealing to occlude flow of liquid therethrough upon removal of the guidewire.

9. The intravascular catheter as in claim 8 wherein the circumferentially spaced cuts are disposed in first and second axially spaced annular bands.

10. The intravascular catheter as in claim 9 wherein the plurality of vibratable flaps deflect liquid in a retrograde direction.

11. The intravascular catheter as in claim 8 wherein the plurality of vibratable flaps deflect liquid in the antegrade direction.

12. The intravascular catheter as in claim 8 wherein the plurality of hinged flaps direct liquid flowing through openings defined by the circumferentially spaced cuts in both an antegrade and a retrograde direction.

13. The intravascular catheter as in claim 1 wherein the circumferentially spaced cuts are disposed in first and second axially spaced annular bands, wherein the first axially spaced annular band has the hinged portion of the vibratable flaps located proximally, wherein the second axially spaced annular band has the hinged portion of the vibratable flaps located distally, and wherein the fluid flow exiting from the vibratable flaps of the first axially spaced annular band is in an opposite direction from the fluid flow exiting from the vibratable flaps of the second axially spaced annular band to collide and create a turbulent broken flow.

14. The intravascular catheter as in claim 1 wherein each of the spaced cuts are three-sided cuts or slits.

15. The intravascular catheter as in claim 14 wherein the three-sided cuts define a generally U-shaped vibratable flaps.

16. The intravascular catheter as in claim 8 wherein the tip member further comprises:
   an outer wall; and
   an inner tubular wall cooperating with the outer wall to define an annular chamber, the annular chamber being in fluid communication with the liquid injected into the lumen, and the inner tubular wall deforming inwardly to close the passageway when the liquid under pressure is injected into the lumen.

17. The intravascular catheter as in claim 16 further comprising:
   a porous, expandable polymer disposed within the annular chamber, the porous, expandable polymer expanding to seal off the passageway when subjected to the liquid under pressure.

18. The intravascular catheter as in claim 8, wherein each of the spaced cuts are three-sided cuts or slits.

19. The intravascular catheter as in claim 18, wherein the three-sided cuts define a generally U-shaped vibratable flaps.

* * * * *